(12) United States Patent
Durisek

(10) Patent No.: US 8,483,552 B2
(45) Date of Patent: Jul. 9, 2013

(54) REMOVABLE HEATER ASSEMBLY FOR A VAPORIZER

(75) Inventor: Niklaus R. Durisek, North Vancouver (CA)

(73) Assignee: West Coast Gifts, Inc., Vancouver (CA)

( * ) Notice: Subject to any disclaimer, the term of this patent is extended or adjusted under 35 U.S.C. 154(b) by 390 days.

(21) Appl. No.: 12/883,740

(22) Filed: Sep. 16, 2010

(65) Prior Publication Data

US 2012/0070134 A1 Mar. 22, 2012

(51) Int. Cl.
*F24F 6/00* (2006.01)
*F27B 14/00* (2006.01)

(52) U.S. Cl.
USPC .......................... 392/386; 392/390; 219/438

(58) Field of Classification Search
USPC ..... 392/386, 390, 391, 392, 393; 128/203.26, 128/203.27; 239/135–139; 131/330, 173
See application file for complete search history.

(56) References Cited

U.S. PATENT DOCUMENTS

| 3,478,300 | A | * | 11/1969 | Griffin | 439/256 |
| 5,084,607 | A | * | 1/1992 | Shafer et al. | 219/270 |
| 6,354,301 | B2 | * | 3/2002 | McCoy | 131/194 |
| 6,761,164 | B2 | * | 7/2004 | Amirpour et al. | 128/203.26 |
| 7,445,007 | B2 | | 11/2008 | Balch et al. | |
| 7,475,684 | B2 | * | 1/2009 | Balch et al. | 128/203.16 |
| 7,624,734 | B2 | | 12/2009 | Balch et al. | |
| 2010/0074603 | A1 | | 3/2010 | Balch et al. | |

FOREIGN PATENT DOCUMENTS

| CA | 2471680 A1 | 12/2005 |
| WO | 2006009923 A2 | 1/2006 |

* cited by examiner

*Primary Examiner* — Sang Paik
*Assistant Examiner* — Renee L Miller
(74) *Attorney, Agent, or Firm* — Wood, Herron & Evans, LLP

(57) ABSTRACT

A removable heater assembly 20 is provided for a vaporizer 10 by which to easily mechanically and electrically connect and disconnect the heater assembly 20 from a base 22 for removal and/or replacement thereof without requiring tools or specialized skills.

11 Claims, 6 Drawing Sheets

REMOVABLE HEATER ASSEMBLY FOR A VAPORIZER

FIELD OF THE INVENTION

The present invention relates to vaporizers, and more particularly, to the heater assembly used in such vaporizers.

BACKGROUND OF THE INVENTION

Vaporizers have been in use for some time for purposes of aromatherapy or to vaporize herb medicaments. The vaporizers typically include a housing supporting a heater assembly. The heater assembly is typically mechanically affixed to the housing and hard-wired into the circuitry of the housing (such as an on/off switch and potentiometer for setting the temperature) so as to be effectively permanently mounted in the housing. Mounted over the heater assembly is a glass tubular member having one or more ports along its side and an opening at its front end to which to couple a negative source of pressure, such as a wand, air hose, or the like. As air is pulled or sucked through the wand, negative pressure is created at the front end of the glass tubular member causing air to enter into the tubular member through the port(s) and to become heated as it passes over the heater assembly therewithin. The heated air exits the glass tubular member to vaporize essential oils or herbal materials associated with the wand. In some uses, an aroma cup may be coupled to the front end of the glass tubular member, and convection current can carry heating air up through the glass tubular member along the heater assembly and into the aroma cup to vaporize essential oils, for example, that may be situated therein.

One problem that adversely affects vaporizers is that the heater assembly can fail or otherwise become damaged such that the vaporizer no longer works effectively, if at all. The vaporizer might be able to be serviced, which involves opening up the vaporizer to gain access to the heater assembly, removing the glass tubular member, and undertaking the work using the proper tool to disconnect the heater assembly, mechanically and electrically, from the housing. A new heater assembly must then be installed and secured in the housing with the proper tools so as to be effectively permanently mounted thereto, and the housing closed up and the glass tubular member reinstalled. That type of repair is time consuming and costly, and is often best left to qualified technicians. Rather than deal with the time, cost, and frustration of seeking service for the vaporizer unit, many users may simply dispose of the vaporizer, perhaps buying a new one. That approach is wasteful and can be costly.

SUMMARY OF THE INVENTION

The present invention provides an easily removable heater assembly and a base for the vaporizer to facilitate the easy removal of the heater assembly without requiring tools thus minimizing or eliminating the need to service, or dispose of, the vaporizer in the event of failure of the heater assembly. To that end, and in accordance with the principles of the present invention, a removable heater assembly is provided which has a generally cylindrical mounting support having an electrical contact tab at one end, and an annular electrical contact band mounted about the support with a generally cylindrical ceramic heater element supported by and extending from the mounting support and electrically coupled to the contact tab and the contact band. The heater assembly can be axially slid into and out of a base associated with the vaporizer to mechanically and electrically connect the heater assembly to the vaporizer and disconnect the heater assembly from the vaporizer, respectively. As a result, the heater assembly is mechanically and electrically connectable and disconnectable without being hardwired, or otherwise being generally permanently mounted, to the vaporizer. Consequently, it is no longer necessary to open up the vaporizer and use tools or require specialized skills to undo or redo what was otherwise considered an effectively permanent mounting in order to remove the heater assembly and replace it with a replacement heater assembly.

In accordance with a further aspect of the present invention, the vaporizer is provided with a base having a receiver portion sized to receive the mounting support of the heater assembly and having an electrical plate contact located along the axis thereof and an electrical clip with an arm astride the axis such that as the mounting support is slid axially into the receiver portion, the annular band makes electrical contact with the arm of the clip, and the tab contact comes into electrical engagement with the plate contact. Thus, the mechanical and electrical connection is made by axially sliding the heater assembly into the receiver portion of the base without using tools or requiring specialized skills. Similarly, the heater assembly is mechanically and electrically disconnected from the vaporizer by axially sliding it out of the receiver portion of the base such as to disconnect the electrical coupling between the annular band and tab contact of the heater assembly with the arm and plate contact of the base, respectively, again without using tools or requiring specialized skills.

In order to better facilitate the easy removal of the heater assembly, the glass tubular member may be removably received to the base, such as by a cooperating threading relationship thereof. To that end, and in accordance with a further aspect of the present invention, removal of the heater assembly is accomplished by unthreading the glass tubular member from the base, pulling the glass tubular member axially out of the vaporizer to expose the heater assembly, axially slidably removing the heater assembly from the base and out of the vaporizer. Replacement is accomplished by axially slidably inserting a replacement heater assembly into the receiver portion of the base for mechanical and electrical connection therewith. Thereafter, either the same glass tubular member or a replacement glass tubular member is axially inserted into the vaporizer over the replacement heater assembly and threadably engaged into the base. The back end of the glass tubular member may be positioned snuggly over the mounting support of the heater assembly to firm up the connection between the heater assembly and the base. The heater assembly is thus easily removed and/or replaced, without the need for qualified service technicians, without the cost or time normally involved in servicing vaporizers to replace a hardwired heater assembly, without requiring tools, and with less risk that the vaporizer will simply be discarded.

By virtue of the foregoing, there is thus provided an easily removable heater assembly and a base for the vaporizer to facilitate the easy removal of the heater assembly without requiring tools to thus minimize or eliminate the need to service, or dispose of, the vaporizer in the event of failure of the heater assembly. These and other objectives and advantages of the present invention will be more readily apparent from the following detailed description of the drawings.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment below, serve to explain the principles of the present invention.

DETAILED DESCRIPTION OF THE INVENTION

Figure 1:
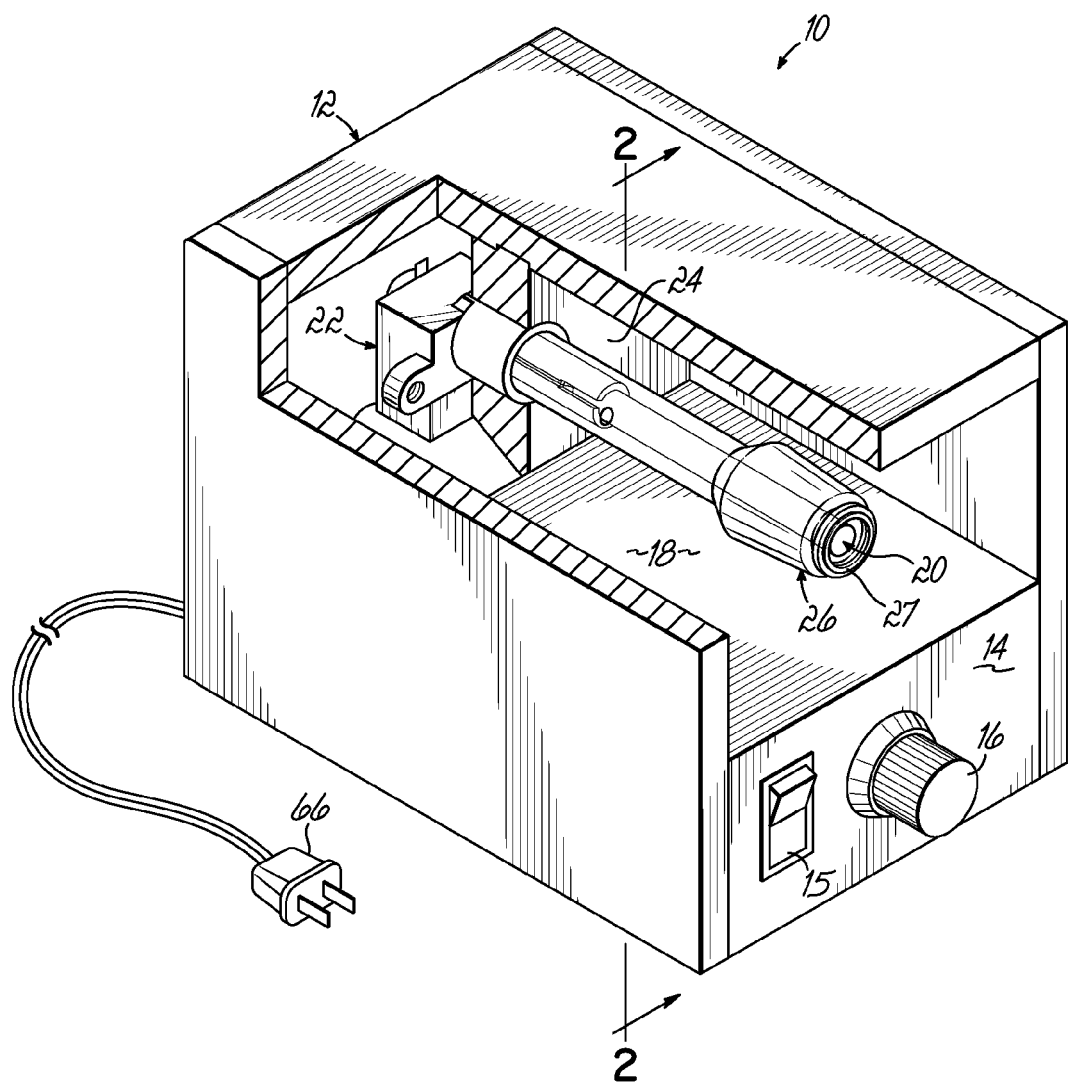
FIG. 1 is a perspective view, partially broken away, of a vaporizer having an embodiment of a removable heater assembly and an embodiment of a base for use therewith in accordance with the principles of the present invention.
Figure 2:
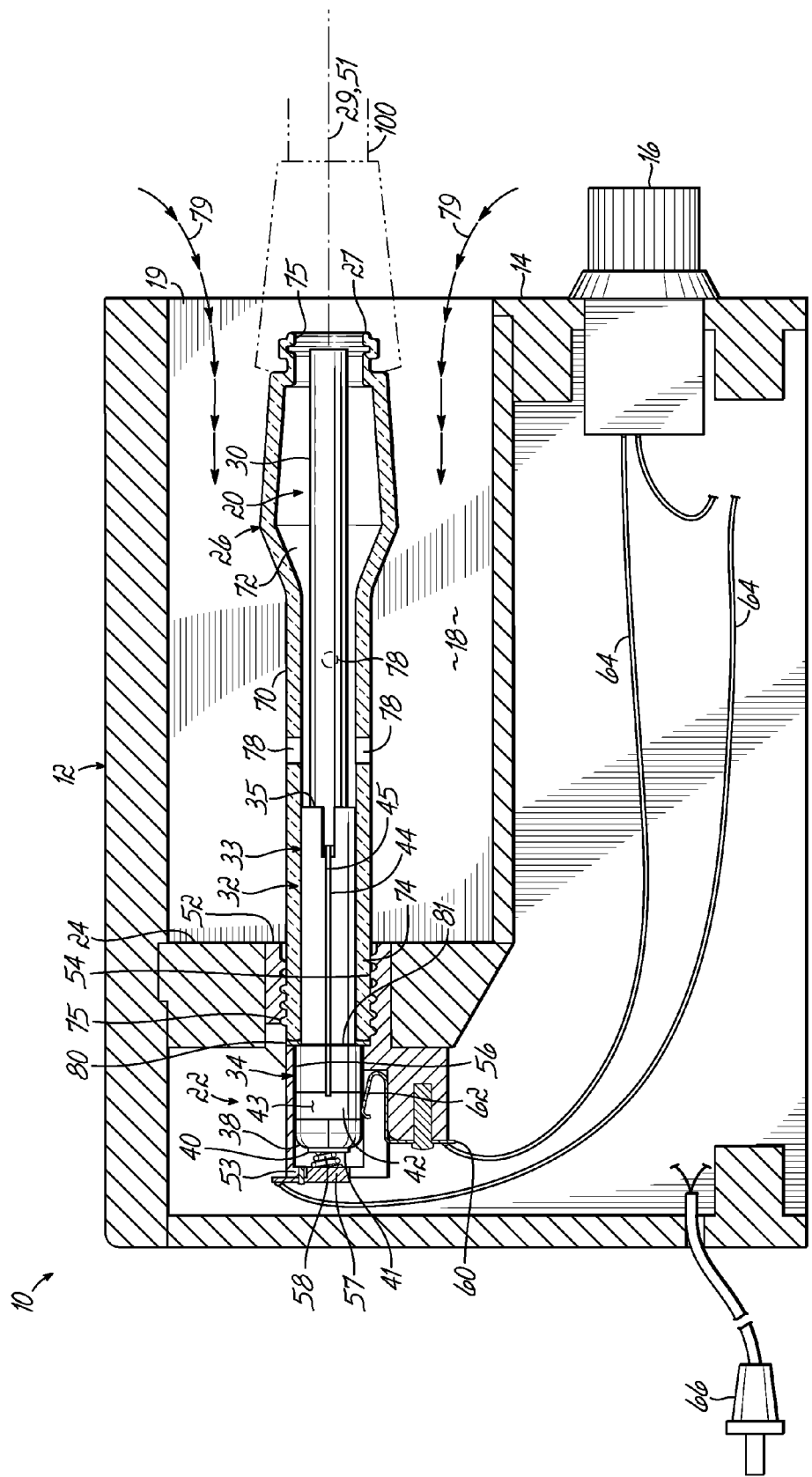
FIG. 2 is a cross-sectional view of the vaporizer of FIG. 1 taken along lines 2-2 of FIG. 1 for purposes of explaining the principles of the present invention.

With reference to FIGS. 1 and 2 there is shown a vaporizer 10 having a housing 12, comprised of wood, plastic, glass, and/or metal and defining a front wall 14 to which is mounted an on/off switch 15 and a potentiometer 16 defining at least in part electric circuitry of vaporizer 10. A heater cavity 18 is defined in housing 12 and is exposed to ambient through front or upper opening 19 adjacent front wall 14. An embodiment of a replaceable heater assembly 20 is mechanically and electrically removably connected to a base 22 secured to a floor or back wall 24 of cavity 18 such that heater assembly 20 extends from floor or back wall 24 towards and adjacent to front or upper opening 19. A glass tubular member 26 is threadably removably connected to base 22 and over heater assembly 20 within cavity 18, with the front end 27 of glass tubular member 26 being accessible at front or upper opening 19.

Figure 3:
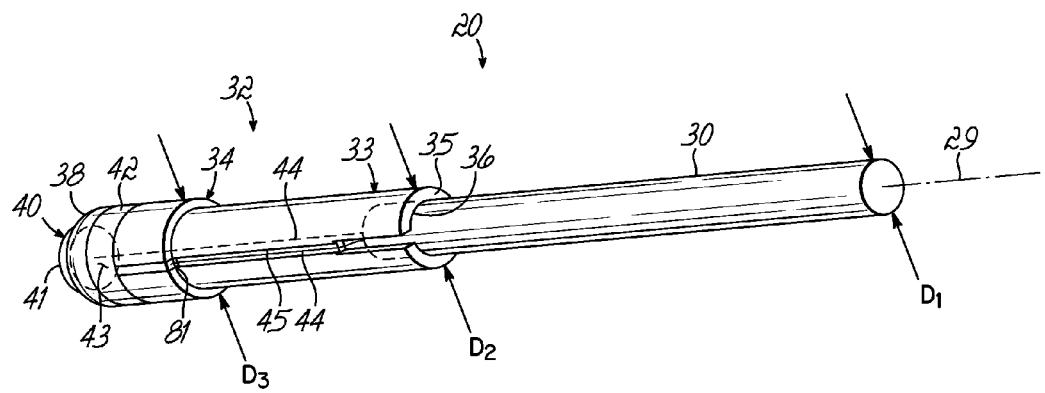
FIG. 3 is a perspective view of the heater assembly of FIG. 1.

With further reference to FIG. 3, heater assembly 20 is elongated along an axis 29 and has an elongated ceramic heating element or rod 30 secured to and supported by a mounting support 32. Ceramic heating element 30 is tubular or cylindrical in cross-section and has a cross-dimension D1, although other shapes may be used. Mounting support 32 is also an elongated member. Mounting support 32 has a front portion 33 and a back portion 34, each having a cross-dimension D2 and D3, respectively, advantageously larger than the cross-dimension D1 of ceramic heating element 30. Ceramic heating element 30 extends into the front end 35 of front portion 33 of mounting support 32 to be secured within a recess 36 thereat. Affixed to the back end 38 of back portion 34 of mounting support 32 is a metal, electrically conductive contact tab 40 that intersects axis 29. Tab 40 may have a planar or slightly outwardly arcuate contact surface 41. Mounted about back portion 34 of mounting support 32 is a metal, electrically conductive annular contact band 42 with a generally smooth contact surface 43 thereabout, spaced from contact surface 41. Tab 40 and band 42 are electrically coupled to ceramic heating element 30 by wires 44 extending into recess 36 (one shown in phantom, the other of which also extends along a grooved recess 45 of mounting support 42 before extending into recess 36). The material of mounting support 32, at least in the area of back portion 34 if not the entire component, is advantageously selected to provide electrical isolation between tab 40 and band 42. To that end, mounting support 32 may advantageously also be comprised of ceramic.

Figure 4:
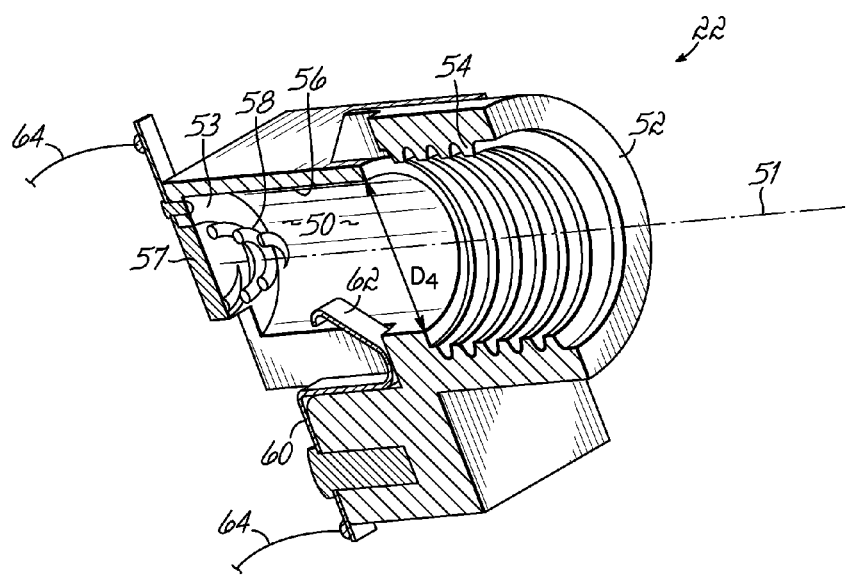
FIG. 4 is a perspective, cross-sectional view, of the base of FIG. 1.

With further reference to FIG. 4, base 22 is formed of translucent plastic, and may have an LED (not shown) mounted into the plastic to illuminate same and/or the glass tubular member 26 mounted thereto. Base 22 has a central aperture 50 with a longitudinal axis 51 extending from a front end opening 52 to a back end 53. Central aperture 50 has a threaded upper portion 54 and a lower tubular or cylindrical receiver portion 56. Receiver portion 56 has an interior cross-dimension D4 closely approximating that of cross-dimension D3 of mounting support 32 such insertion of second portion 34 of mounting support 32 through opening 52 and into receiver portion 56 brings them in snug, receiving relationship to provide mechanical support for heater assembly 20. Secured adjacent back end 53 is a metal, electrically conductive plate contact 57 along or intersected by longitudinal axis 51, and which may include a metal spring 58, by which to make sliding electrical engagement with surface 41 of tab 40 with heater assembly 20 mechanically removably connected to base 22. Base 22 also includes a metal, electrically conductive clip 60 having a contact wiper arm 62 extending into receiver portion 56 astride axis 51 by which to bear against and be flexed radially outwardly by mounting support second portion 34 as it is inserted into receiver portion 56, and to slidingly engage into contact with annular contact 42 when or as the second portion 34 is seated in receiver portion 56. Plate contact 57 and clip 60 are electrically hard-wired to on/off switch 15 and/or potentiometer 16 via wires 64 (FIG. 2) secured thereto by screws and/or soldering, by which to selectively control the power level to heater assembly 20 when vaporizer 10 is plugged in, such as through plug 66. As can thus be seen, base 22 also serves as a power connector for ceramic heating element or rod 30, with surfaces 41 and 43 making sliding electrical engagement with plate contact 57 (such as via spring 58) and clip 60 (such as via arm 62).

With reference again to FIGS. 1 and 2, glass tubular member 26 is advantageously removably coupled to base 22 so as to extend over heater assembly 20, or at least ceramic heating element 30 thereof, if not also front portion 33 of the mounting support 32. To that end, glass tubular member 26 has a tubular sidewall 70 defining an interior airway path 72 therethrough and which is sized larger than the cross-dimension D1 of ceramic heating element 30, but adjacent the back end 74 of member 26 is sized to closely match to the cross-dimension D2 of front portion 33 of mounting support 32. The back end 74 of member 26 is provided with exterior threads 75 sized to threadably engage threaded upper portion 54 of base 22 by which to mechanically mount glass tubular member 26 to vaporizer 10 with the heater assembly 20 extending into airway path 72, but stopping short of the opening 75 at the front end 27 of member 26. The size of the back end 74 provides a snug fit between the back end 74 and the mounting support 32 so as to firm up the connection between the mounting support 32 of the heater assembly 20 and the base 22 when member 26 is threadably engaged into upper portion 54 of base 22. Member 26 also has one or more ports 78 extending through sidewall 70 to communicate with airway path 72. Advantageously, a spring steel washer 80 is provided at the intersection 81 of portions 33, 34 of mounting support 32 to fit between back end 74 of member 26 and the intersection 81.

In use, negative pressure may be applied at opening 75, such as by sucking air through a wand 100 (FIG. 2, only a portion is shown, in phantom) or other similar device coupled to front end 27, air (as exemplified by arrows 79) is pulled into cavity 18 through at least front or upper opening 19, and into airway path 72 via port(s) 78 to be heated as it passes along ceramic heating element 30 to thus provide heated, vaporizing air at opening 75.

Figure 5A:
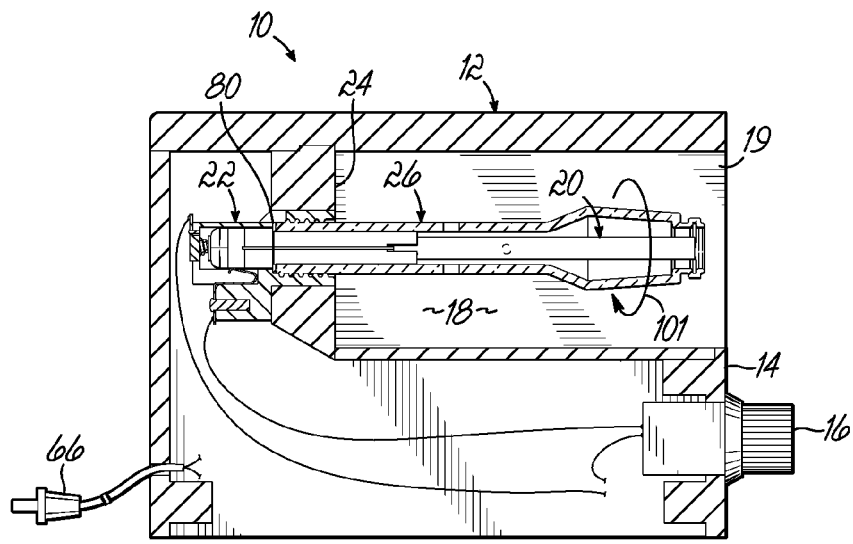
FIGS. 5A through 5F are views similar to FIG. 2 showing a method of replacing the heater assembly of FIG. 1.
Figure 5B:
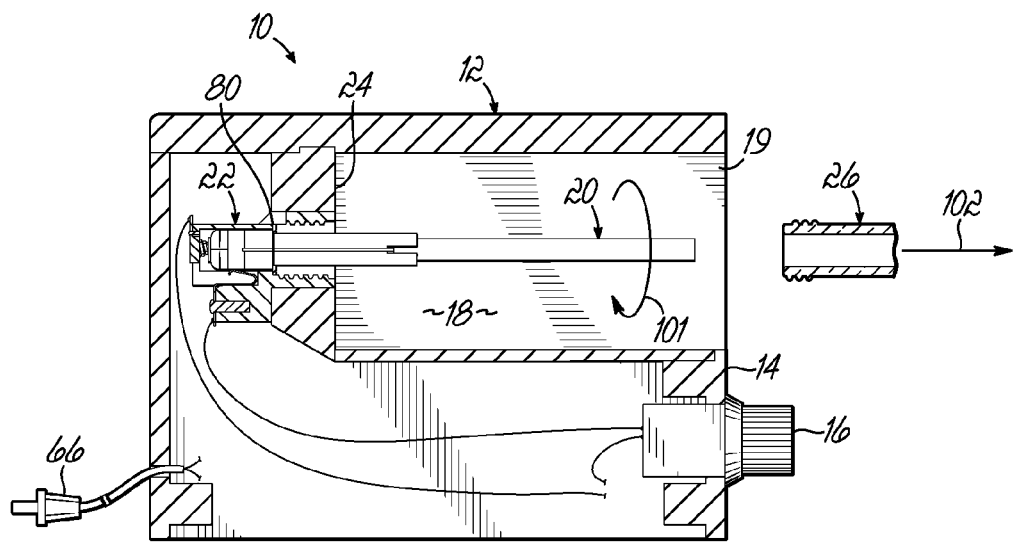
Figure 5C:
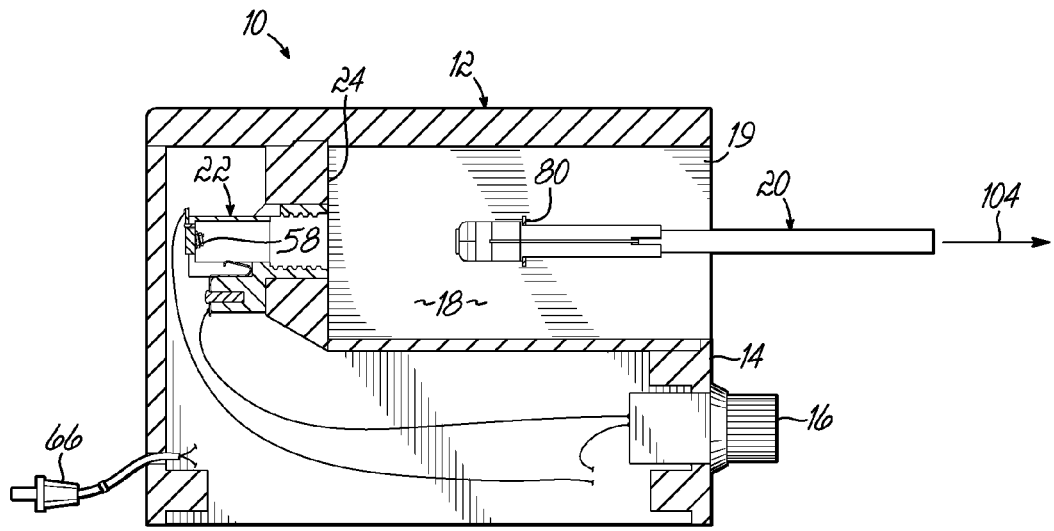
Figure 5D:
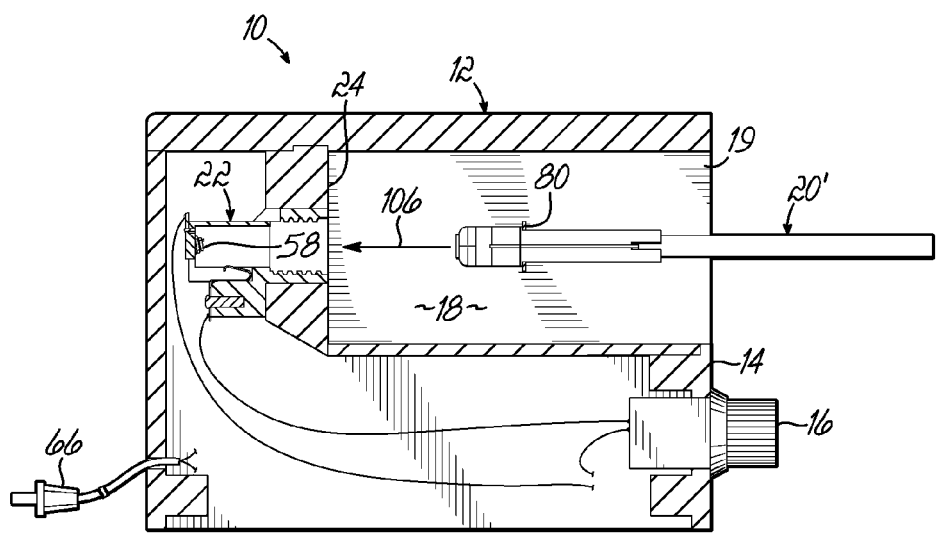
Figure 5E:
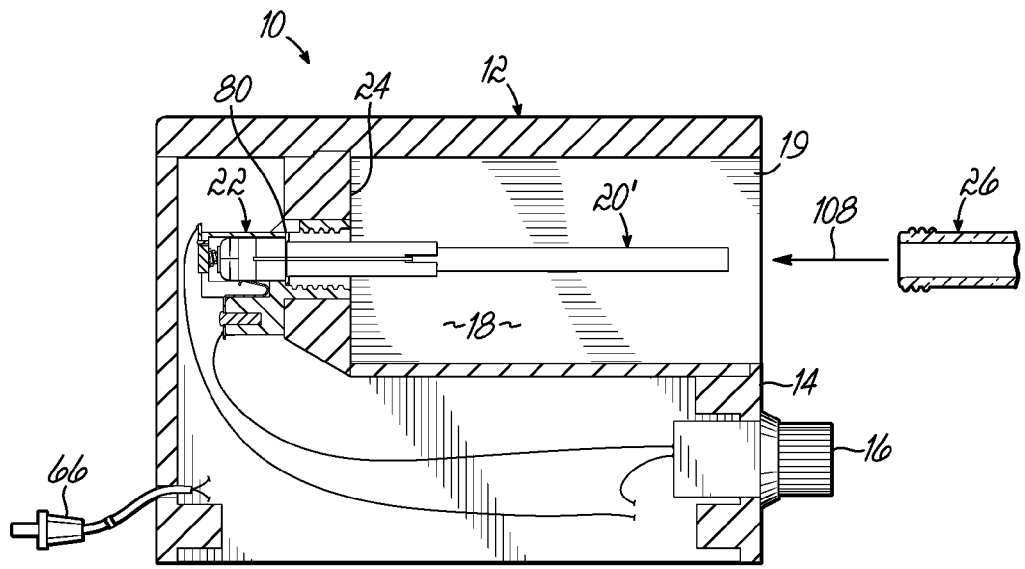
Figure 5F:
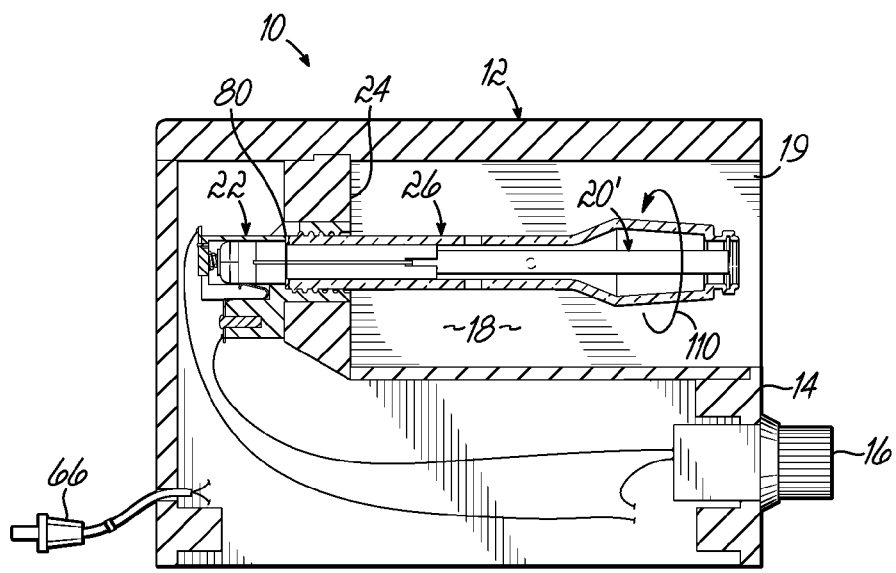

During use, heater assembly 20 can fail or otherwise become damaged. Rather than undertaking the time and expense of a full-blown service of vaporizer 10, or simply discarding same, the present invention provides a method of simple heater assembly removal and replacement. To that end, and with reference to FIGS. 5A through 5F, should it be necessary to remove heater assembly 20, a user (not shown) can easily do so by (a) threadably disconnecting glass tubular member 26 from base 22 such as by unscrewing member 26 from threaded upper portion 54 of base 22 as exemplified by arrow 101 in FIG. 5A, (b) pulling member 26 out of cavity 18 of vaporizer 10 as along arrow 102 to expose heater assembly 20 as exemplified in FIG. 5B, (c) mechanically and electrically disconnecting heater assembly 20 from vaporizer 10 such as by slidably withdrawing heater assembly 20 axially from cavity 18 along arrow 104 as exemplified in FIG. 5C. The foregoing can be done without tools and without requiring a specialized or skilled technician. The user can then easily replace the heater assembly 20 by inserting a replacement heater assembly 20' into the vaporizer 10 (along with the washer 80 or a new washer 80 mounted thereover), such as by axially slidably inserting same along arrow 106 sufficient to bring its rear portion 34 into a mechanically snug fit with receiver portion 56, such that plate contact 57 (such as via spring 58 if present) and clip 60 (such as via arm 62) are slidingly engaged into electrical contact with tab 40 and annular contact 42 (and their respective surfaces 41, 43) as exemplified by FIG. 5D. Finally, glass tubular member 26 (or a replacement) may be remounted to vaporizer 10 by inserting same axially into cavity 18 as along arrow 108 over replacement heater assembly 20' (FIG. 5E) and connecting same to base 22 (FIG. 5F) such as by threading them together by rotating member 26 as along arrow 110. Advantageously, plug 66 was first disconnected from its outlet (not shown), or at least on/off switch 15 was placed in the "off" position during the removal and/or replacement process, and plug 66 is reconnected and/or the unit switched on for use only after the process is completed. Further, it may not be necessary to first remove glass tubular member 26 if it has previously been removed thus exposing heater assembly 20 for other reasons.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, while vaporizer 10 is shown with axes 29 and 51 being on the horizontal, they could be on the vertical or at an angle therebetween. Also, a screen (not shown) may be inserted at opening 75 of glass tubular member 26. Additionally, other known electrical connections may be utilized to couple heater assembly 20 and base 22, such as plug and socket arrangements known in the electrical arts to provide slidingly engagable electrical surfaces and/or contacts. Other heater assembly and base designs may also be utilized as will be readily apparent to those skilled in the art. It will also be appreciated that while tools are not required to remove and/or replace the heater assembly, tools can be used if desired. Advantageously, member 26 and/or heater assembly 20 are not removed while they are still hot. In any event, a rag or the like may advantageously be used to grip member 26 and/or heater assembly 20 during removal, for example, but such rag or the like is not considered a tool as that term is used herein. Further, while on/off switch 15 and potentiometer 16 are shown as separate elements, they could be combined into a single unit. The invention in its broader aspects is therefore not limited to the specific details, representative apparatus and methods shown and described. Accordingly, departures may be made from such details without departing from the scope or spirit of applicant's general inventive concept.

Having described the invention, what is claimed is:

1. A removable heater assembly for a vaporizer comprising:
   a generally cylindrical mounting support comprised of electrically isolating material
   extending between first and second ends and having a back portion of a fixed cross-dimension
   disposed near the first end, an electrical contact tab associated with the first end, and an annular
   electrical contact band mounted about the support in the back portion thereof so as to define
   annular bands of electrically isolating material of the fixed cross-dimension to either side of the
   electrical contact band whereby to define a substantially constant diameter of the back portion, and
   a generally cylindrical ceramic heating element supported to extend from the mounting
   support second end, and electrically coupled to the contact tab and the contact band, whereby the heater assembly can be axially slid into and out of a base associated with said vaporizer to
   mechanically and electrically connect the heater assembly to said vaporizer and disconnect the
   heater assembly from said vaporizer, respectively.

2. The removable heater assembly of claim 1, the mounting support having a cross-dimension larger than a cross-dimension of the ceramic heating element.

3. The removable heater assembly of claim 2, the mounting support having first and second portions each having a respective cross-dimension larger than the cross-dimension of the ceramic heating element and extending, respectively, from the first and second ends, the cross-dimension of the first portion being larger than the cross-dimension of the second portion, the annular contact being mounted on the first portion.

4. The removable heater assembly of claim 1, the mounting support having first and second portions each having a respective cross-dimension and extending, respectively, from the first and second ends, the cross-dimension of the first portion being larger than the cross-dimension of the second portion, the annular contact being mounted on the first portion.

5. A removable heater assembly for a vaporizer comprising an elongated heater assembly
   having an elongated ceramic rod and a power connector electrically and mechanically coupled to
   an end of the ceramic rod to support and couple power to the ceramic rod, the ceramic rod
   heating up on application of power to the power connector, the power connector having exposed,
   spaced electrical contact surfaces adapted to slidingly engage with electrical contacts of said
   vaporizer, a back portion of the power connector being comprised of electrically isolating
   material and having a fixed cross-dimension, one of the electrical contact surfaces being
   positioned along the power connector portion so as to define respective portions of electrically
   isolating material of the fixed cross-dimension to either side of the one electrical contact band
   whereby to define a substantially constant diameter of the back portion, such that the elongated
   heater assembly may be slidably attached to vaporizer electrical contacts through which to apply
   power to the power connector and such that the elongated heater assembly may be slidably removed from said vaporizer for replacement, whereby the elongated heater assembly is not hard-wired to the vaporizer to facilitate ready replacement in the field.

6. In a vaporizer having a base therein, an elongated heater assembly coupled to the base in the vaporizer, and a glass tubular member coupled to the base in the vaporizer, the elongated heater assembly and glass tubular member extending from the base with the elongated heater assembly extending into a central lumen of the glass tubular member, a method comprising threadably disconnecting the glass tubular cylinder from the base, pulling the glass tubular member out of the vaporizer to expose the elongated heater assembly, and mechanically and electrically disconnecting the elongated heater assembly from the vaporizer by slidably withdrawing the elongated heater assembly axially from the vaporizer without using tools.

7. The method of claim 6 further comprising slidably inserting a replacement elongated heater assembly into the vaporizer sufficient to mechanically and electrically connect the replacement elongated heater assembly element to the vaporizer without using tools.

8. The method of claim 7 further comprising inserting the glass tubular member axially into the vaporizer over the replacement elongated heater assembly and threadably attaching the glass tubular member to the vaporizer.

9. The method of claim 8 further comprising first associating a washer with the replacement elongated heater assembly before inserting the glass tubular member into the vaporizer.

10. The method of claim 7 further comprising inserting a replacement tubular glass member axially into the vaporizer over the replacement elongated heater assembly and threadably attaching the replacement glass tubular member to the vaporizer.

11. The method of claim 10 further comprising first associating a washer with the replacement elongated heater assembly before inserting the replacement glass tubular member into the vaporizer.

* * * * *